(12) United States Patent
Perring et al.

(10) Patent No.: US 6,231,846 B1
(45) Date of Patent: May 15, 2001

(54) HAIR TREATMENT COMPOSITIONS CONTAINING REDUCING SULPHUR SPECIES AND ZINC COMPOUND

(75) Inventors: Keith Douglas Perring; Philip William Goulding, both of Ashford (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/388,376

(22) Filed: Sep. 1, 1999

Related U.S. Application Data

(63) Continuation of application No. PCT/GB98/00640, filed on Mar. 2, 1998.

(30) Foreign Application Priority Data

Mar. 3, 1997 (EP) .................................................. 97301401

(51) Int. Cl.⁷ .................................................. A61K 7/155
(52) U.S. Cl. ........................ 424/73; 424/70.2; 424/70.4; 424/70.5
(58) Field of Search ................... 424/70.4, 70.5, 424/70.51, 70.2, 73, 70.1, 641, 703

(56) References Cited

U.S. PATENT DOCUMENTS 5,051,252    9/1991    Schultz et al. .......................... 424/71

FOREIGN PATENT DOCUMENTS

| 218 931 | 4/1987 | (EP) . |
| 622 109 | 11/1994 | (EP) . |
| 674195 | 6/1952 | (GB) . |
| 91/02538 | 3/1991 | (WO) . |

OTHER PUBLICATIONS

Chemical Abstract, vol. 122, No. 18, May 1, 1995, Columbus, Ohio, US; abstract No. 221603 K. ARAI: "Deodorants containing metal oxides for efficient removal of various malodor" XP002036850 see abstract & JP 07 016 422 A (Kobe Steel Ltd.) Jan. 20, 1995.

*Primary Examiner*—James M. Spear
(74) *Attorney, Agent, or Firm*—Pillsbury Winthrop LLP

(57) ABSTRACT

Hair treatment compositions, such as depilatory products and hair straightening and permanent waving products, containing reducing sulphur species, particularly thioglycolates, additionally incorporate zinc compounds, particularly zinc oxide, to reduce malodor.

11 Claims, 2 Drawing Sheets

HAIR TREATMENT COMPOSITIONS CONTAINING REDUCING SULPHUR SPECIES AND ZINC COMPOUND

This application is a continuation of PCT/GB98/00640 filed Mar. 2, 1998.

FIELD OF INVENTION

This invention concerns hair treatment compositions such as depilatory products and hair straightening and permanent waving products.

BACKGROUND TO THE INVENTION

Hair treatment compositions such as depilatory products and hair straightening and permanent waving products typically contain reducing sulphur species such as sulphides and thioglycolates, with depilatory products commonly including calcium thioglycolate and hair straightening and permanent waving products commonly including ammonium thioglycolate. The reducing sulphur species generate a variety of sulphur-containing volatiles, including hydrogen sulphide, methanethiol, dimethyl sulphide and dimethyl trisulphide, which are present at low levels in air above such products. This results in an unpleasant odour, which increases substantially during use, which can be offensive to users.

The present inventors have surprisingly found that incorporating zinc compounds, particularly zinc oxide, in such hair treatment compositions substantially reduces malodour production, both on storage and in use.

SUMMARY OF THE INVENTION

Accordingly, the present invention provides a hair treatment composition containing reducing sulphur species, wherein the composition also includes a zinc compound.

The invention is applicable to a range of hair treatment compositions containing reducing sulphur species, particularly thiol compounds such as thioglycolates. For example, the invention is applicable to depilatory compositions (eg in milk, cream, lotion or gel form) including thioglycolate, particularly calcium thioglycolate, which typically have a pH of about 12.5. The invention is also applicable to hair straightening and permanent waving compositions (eg in lotion form) including thioglycolate, particularly ammonium thioglycolate, which typically have a pH in the range 7 to 9.5.

The zinc compound may be a zinc salt such as zinc carboxylate eg zinc acetate, zinc chloride etc. Preferably, however, the zinc compound is zinc oxide. A mixture of zinc compounds may be used, but it is preferred to use zinc oxide alone.

We have found that during depilation using thioglycolate-based depilatories, substantial quantities of one sulphur-containing volatile are evolved. Gas chromatographic (gc) and mass spectral (ms) analyses have identified this material as methanethiol. Other substances are likely also to contribute towards the perceived malodour in-use, but nevertheless methanethiol lies at the heart of the problem.

We have similarly found that methanethiol is also liberated during hair relaxation using thioglycolate-based perming products, although in this case there is additionally a substantial amount of hydrogen sulphide present (possibly as a result of the much lower pH compared with depilatories, typically 7 to 9.5 versus 12.5 in depilatories). As with depilatories other materials may play a part in the in-use malodour.

Gc analysis of headspace gas above thioglycolate-based hair treatment products, with and without zinc compounds, has shown that the presence of zinc compounds, particularly zinc oxide, substantially reduces the production of methanethiol. Subjective odour evaluation tests showed a corresponding reduction in malodour with products including zinc compounds, both on storage and in use.

The zinc compound, preferably zinc oxide, is suitably present in an amount in the range 0.05 to 15%, preferably 0.1 to 10%, more preferably 0.2 to 5%, most preferably 0.3 to 3%, typically about 0.5%, of the total weight of the composition.

The composition may include one or more fragrance ingredients, as is conventional in hair treatment compositions. It is surprisingly found that use of one or more acetal fragrance ingredients is particularly effective in reducing malodour production. Typical examples of acetal fragrance ingredients are:

1-(ethoxymethoxy)cyclododecane
4,4a,5,9b-tetrahydroindeno[1,2-α][1,3]dioxine
5-(sec-butyl)-2-(2,4dimethyl-3-cyclohexenyl)-5-methyl-1,3-dioxane
2-(1-ethylpentyl)-1,3-dioxolane
1-(2,2dimethoxyethyl)benzene
2-Isobutyl-5-methyl-1,3-dioxane
2-(1-phenylethyl)-4-methyl-1,3-dioxolan
1-(2,2-dimethoxy-1-methylethyl)benzene A perfume formulation for use with such hair treatment compositions will typically contain a number of different fragrance ingredients. In accordance with the invention it is preferred to use a perfume formulation containing at least 5% by weight of acetal fragrance ingredient or ingredients, eg one or more of those listed above.

An example of a preferred perfume formulation, containing a mixture of ingredients in hedonic accord with one another and which are reasonably stable in thioglycolate base, is as follows:

|  | % w/w |
| --- | --- |
| Boisambrene Forte (Henkel) (acetal) | 5.0 |
| Florosa (Quest) | 5.0 |
| Indolal 10% in DPG (Dragoco) (acetal) | 0.5 |
| Jasmacyclene (Quest) | 1.5 |
| Jasmopyrane Forte (Quest) | 3.0 |
| Lily Aldehyde (Bush Boake Allen) | 10.0 |
| Methyl dihydrojasmonate (Quest) | 20.0 |
| Phenyl ethyl alcohol | 15.0 |

The perfume formulation is suitably present in an amount in the range 0.1 to 2%, preferably 0.2 to 1%, of the total weight of the composition.

In a preferred aspect the invention thus provides a hair treatment composition comprising thioglycolate, zinc oxide and at least one acetal fragrance ingredient.

The composition generally also includes other ingredients appropriate to the type of hair treatment, as is known to those skilled in the art.

The invention also includes within its scope a method of reducing malodour of hair treatment compositions containing reducing sulphur species, comprising adding a zinc compound, preferably zinc oxide.

The invention will be further described, by way of illustration, in the following Examples and with reference to the accompanying figures in which:

EXAMPLE 1

Experiments were carried out using an unperfumed gel depilatory formulation having the following composition:

| | |
|---|---|
| Potassium thioglycolate (30% aq.) | 10.0% |
| Sodium hydroxide | to pH 12.5 |
| Structure 2001 * | 5.0% |
| Urea | 8.0% |
| Purified water | to 100 |

* Stabiliser (available from National Starch)

Gas headspace measurements were made by gas chromatography using sulphur-selective detection of methanethiol production during depilation, using the depilatory formulation alone and the depilatory formulation to which had been added 0.5% by weight of various materials, including zinc oxide.

The methanethiol headspace value for the depilatory formulation alone was taken as 100. Comparative values for formulations with additives were as follows:

| Material | Methanethiol Headspace |
|---|---|
| Boisambrene Forte # | 75 |
| Indolal ## | 84 |
| ZnO | 6 |
| TiO$_2$ | 95 |
| Lead diacetate | 75 |
| Zinc acetate | 42 |

Boisambrene Forte is 1-(ethoxymethoxy)cyclododecane
Indolal is 4, 4a, 5, 9b-tetrahydroindeno[1, 2-α][1, 3]dioxine These results show that while all of the added materials reduced methanethiol production to some extent, zinc oxide was substantially more effective than the other materials.

EXAMPLE 2

Figure 1A:
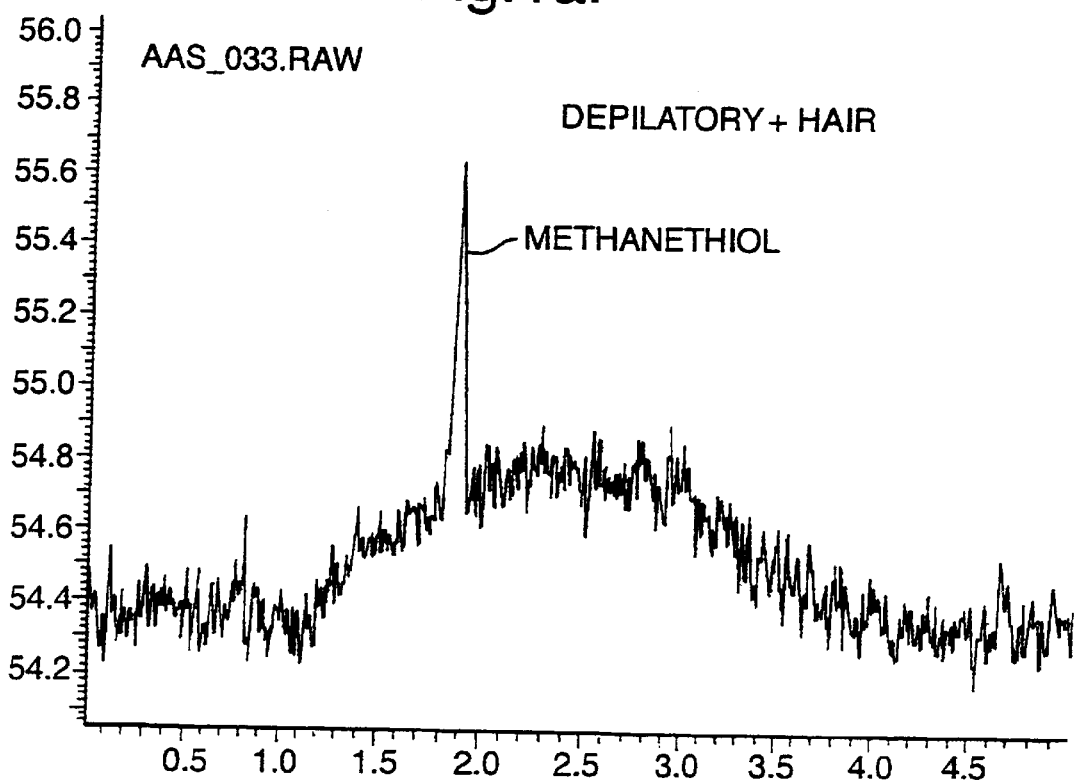
FIG. 1 is a pair of gas chromatography traces.
Figure 1B:
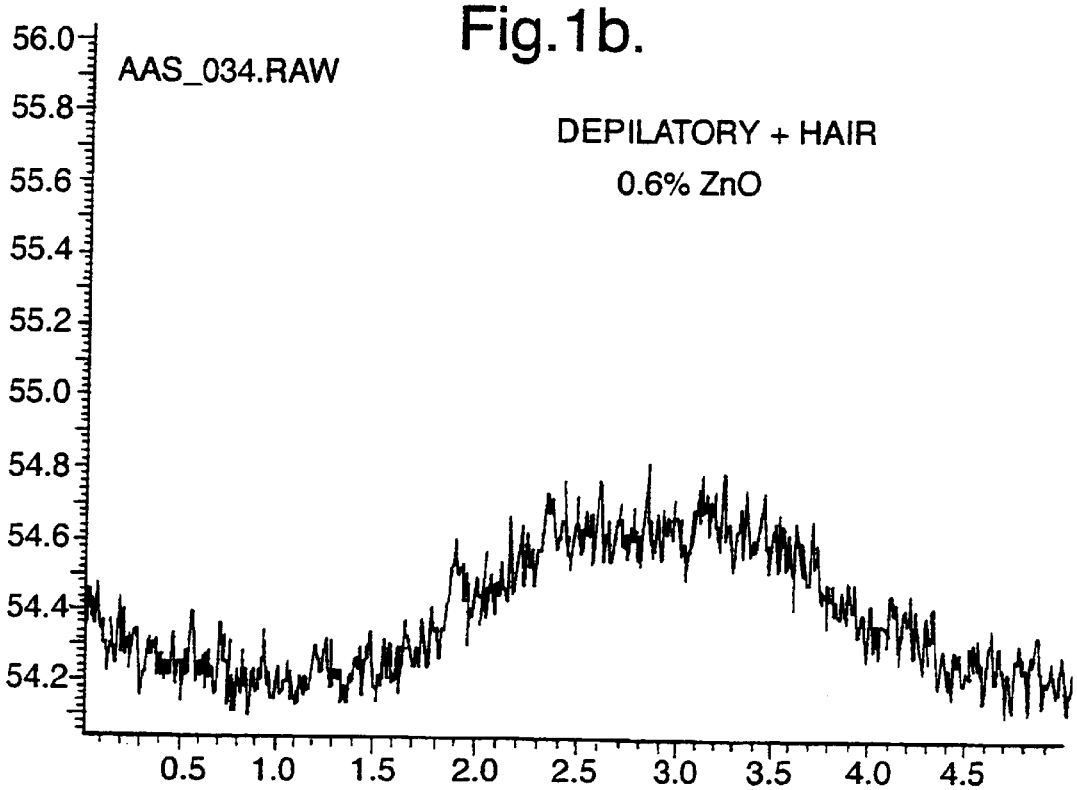

Experiments similar to those of Example 1 were carried out using the same unperfumed gel depilatory formulation, with and without 0.6% zinc oxide. Gas chromatography measurements were made of methanethiol production during depilation. FIG. 1 shows gas chromatography traces obtained in this way, with FIG. 1a showing results for the formulation without zinc oxide. This gc trace includes a marked methanethiol peak. FIG. 1b shows comparable results for the formulation with 0.6% zinc oxide. In this case there is no corresponding methanethiol peak.

EXAMPLE 3

Further experiments were carried out using the same unperfumed gel depilatory formulation, with and without 0.6% zinc oxide, as in Example 2. Subjective odour assessments were made by 6 different assessors during depilation, using 0.125 g hair and 5 g gel base, assessed 3 minutes after application. The assessors adopted a malodour intensity control value of 5 for the depilatory formulation alone. Results of assessments for formulation with zinc oxide were as follows:

| Assessor | Malodour Intensity |
|---|---|
| 1 | 1 |
| 2 | 2 |
| 3 | 2 |
| 4 | 1 |
| 5 | 2 |
| 6 | 1 |

These subjective results indicate that zinc oxide significantly reduces malodour, and generally parallel the gc results of methanethiol levels.

EXAMPLE 4

Figure 2A:
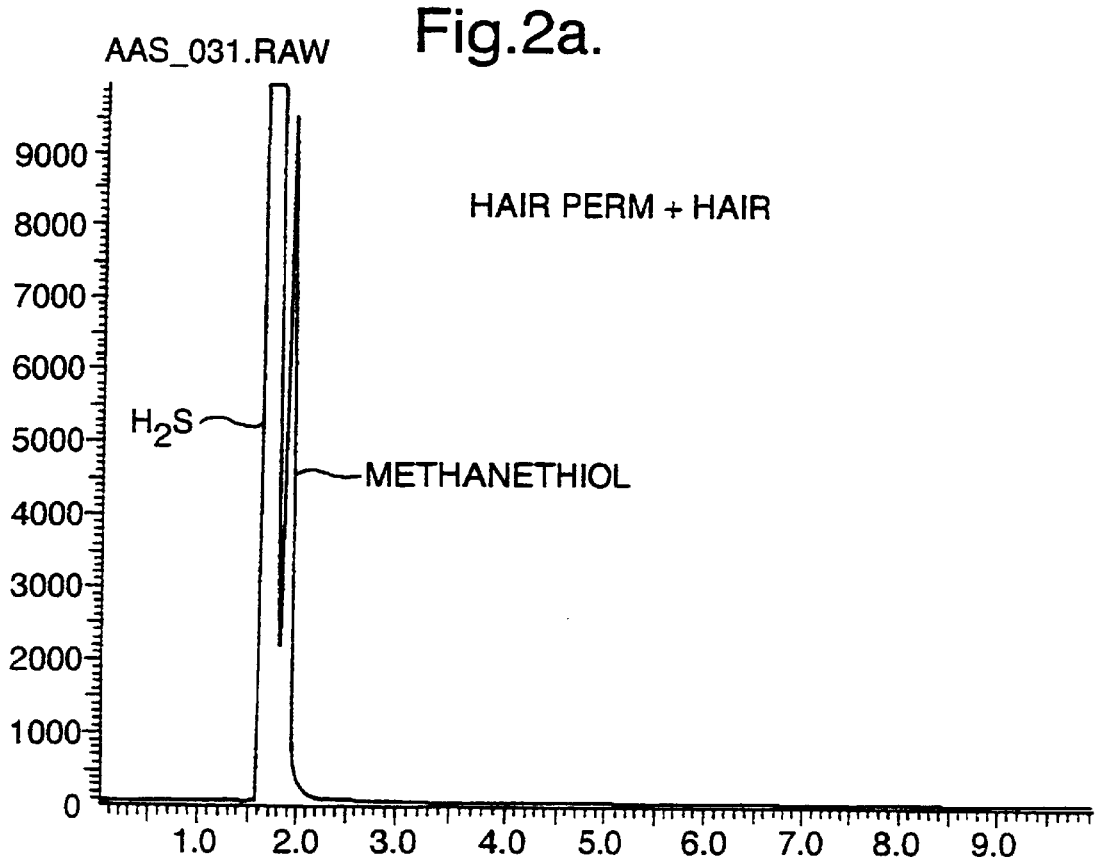
FIG. 2 is a further pair of gas chromatography traces.
Figure 2B:
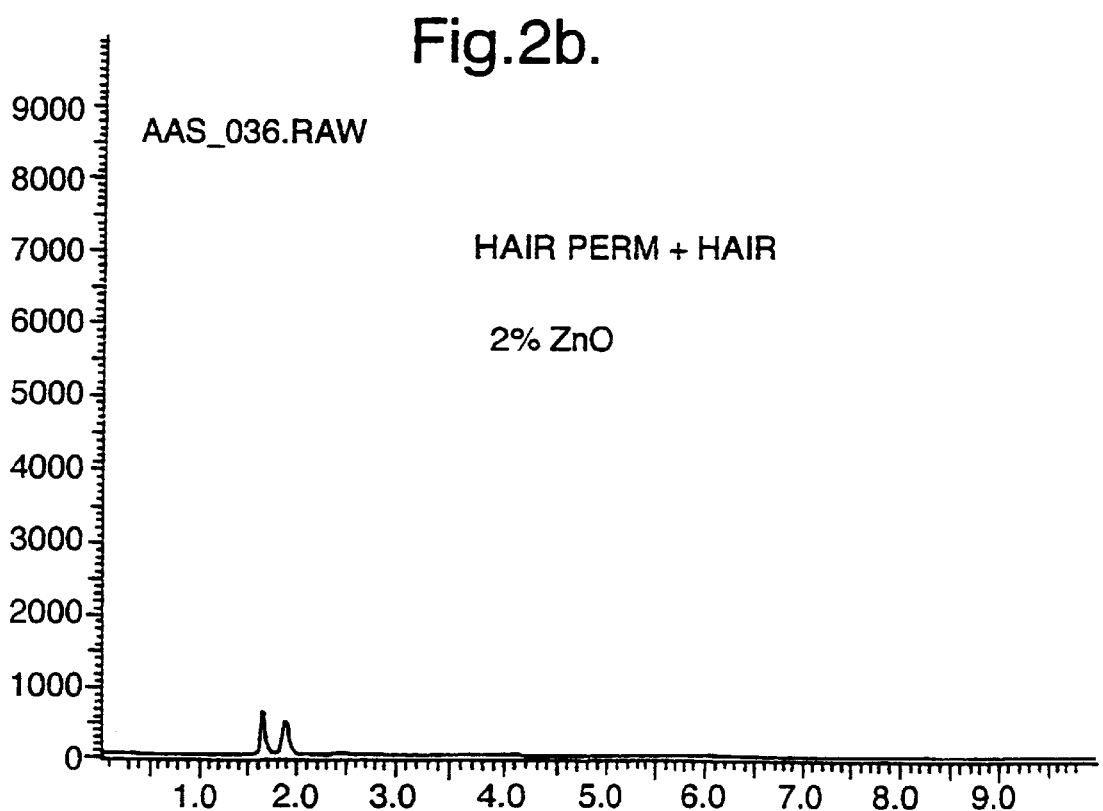

Experiments similar to those of Example 2 were carried out, using the clear hair perming lotion described in Example 7, with and without 2% by weight of zinc oxide. FIG. 2 shows gc traces, showing peaks for hydrogen sulphide (first peak) and methanethiol (second peak) produced during hair relaxation using the perming product without zinc oxide (FIG. 2a) and with zinc oxide (FIG. 2b). Both peaks are substantially reduced for the lotion with zinc oxide.

EXAMPLE 5

A fast acting depilatory cream suitable for use on both the face and the body to remove unwanted hair, and incorporating zinc oxide in accordance with the invention, was made as follows.

| Formulation: | % w/w |
|---|---|
| Phase A: | |
| Purified water | to 100.00 |
| Empicol ESB 3 (i) | 0.50 |
| Tetrasodium EDTA | 0.50 |
| Phase B: | |
| Light Mineral Oil (ii) | 3.00 |
| Laurex CS (iii) | 10.00 |
| Phase C: | |
| Calcium thioglycolate | 7.00 |
| Calcium hydroxide | 5.00 |
| Purified water | 30.00 |
| Phase D: | |
| Quest Fragrance | as required |

(i) Empicol ESB 3 is sodium lauryl ether (2 mol) sulphate, 27% active, from Albright & Wilson. The INCI adopted name is sodium laureth sulfate.
(ii) Suitable grades of light mineral oil are those known by the Trade Names Carnation or Klearol from Witco Corporation.
(iii) Laurex CS is a mixture of fatty alcohols, predominately cetyl and stearyl alcohols from Albright & Wilson. The INCI adopted name is cetearyl alcohol.

Preparation

Heat phase A and phase B, separately to 70° C. Add phase A to B with rapid agitation. Allow to cool with stirring. When the temperature reaches 40° C. add phase C, followed by phase D. 0.5% zinc oxide was then added.

EXAMPLE 6

A glossy, white depilatory cream suitable for use on both the face and body to remove unwanted hair, and incorporating zinc oxide in accordance with the invention, was made as follows:

| Formulation | % w/w |
|---|---|
| Phase A: | |
| Dehydag Wax N (i) | 4.00 |
| Eumulgin B3 (ii) | 2.00 |
| Phase B: | |
| Purified water | to 100.00 |
| Urea | 4.00 |
| Tetrasodium EDTA | 0.50 |
| Phase C: | |
| Purified water | 40.00 |
| Thioglycollic acid | 6.00 |
| Lithium hydroxide | 4.50 |
| Phase D: | |
| Quest Fragrance | as required |

(i) Dehydag Wax N is self-emulsifying cream base material from Henkel. The INCI adopted name is cetearyl alcohol (and) sodium cetearyl sulfate.
(ii) Eumulgin B3 is an oil in water, non-ionic emulsifier from Henkel. The INCI adopted name is Ceteareth-30.

Preparation

Heat phases A and B, separately, to 70° C. Add phase B to phase A with rapid stirring. Continue stirring until the cream cools to under 40° C., before adding phase C. Add phase D, and mix until homogenous. 0.5% zinc oxide was then added.

EXAMPLE 7

Permanent waving lotions, incorporating zinc oxide in accordance with the invention, were prepared as follows. The lotions are referred to as GT 553A, which is an opacified lotion, and GT 553B, which is clear.

| Formulation | GT553A % w/w | GT 553B % w/w |
|---|---|---|
| Phase A: | | |
| Ammonium thioglycolate (40% Solution) (from Robinsons Bros) | 23.30 | 23.30 |
| Purified water | to 100.00 | to 100.00 |
| Opacifying Latex E-295 (ii) From Morton Chemical (The INCI name is sodium styrene/ acrylates/divinyl benzene copolymer (and) ammonium nonoxynol-4 sulfate) | 0.10 | |
| Phase B: | | |
| Ammonia 0.880 S.G. | 0.70 | 0.70 |
| Ammonium bicarbonate (Ammonium hydrogen carbonate) | 2.00 | 2.00 |
| Phase C: | | |
| Quest Fragrance | as required | |
| Fragrance Solubiliser Cremaphor RH40 or RH60 from BASF | as required | |
| Dye eg Ext. D&C Yellow No. 7 (CI No. 45350) and Rhodamine B (CI No. 45170) | as required | |

Preparation

Disperse the opacifying latex in the water (if applicable). Add the ammonium thioglycolate to the water with stirring. Add the ammonia slowly and carefully to this mixture with stirring, followed by the ammonium bicarbonate. Ensure that all the ammonium bicarbonate has dissolved. Finally, when cool add the fragrance, premixed with the solubiliser, to the lotion. A stable dye may be added if required. 2% of zinc oxide was added.

What is claimed is:

1. A hair treatment composition containing reducing sulphur species, a zinc compound and at least one acetal fragrance.

2. A composition according to claim 1, comprising a depilatory composition including thioglycolate.

3. A composition according to claim 1, comprising a hair straightening or permanent waving composition including thioglycolate.

4. A composition according to claim 1, wherein the zinc compound is zinc oxide.

5. A composition according to claim 1, wherein the zinc compound is present in an amount in the range 0.05 to 15%, of the total weight of the composition.

6. A hair treatment composition comprising thioglycolate, zinc oxide and at least one acetal fragrance ingredients.

7. A method reducing malodour of hair treatment compositions containing reducing sulphur species and a zinc compound which comprises adding to said composition at least one acetal fragrance.

8. A composition according to claim 5 wherein the zinc compound is present in an amount of from 0.1 to 10% of the total weight of the composition.

9. A composition according to claim 5 wherein the zinc compound is present in an amount of from 0.3 to 3% of the total weight of the composition.

10. A composition according to claim 5 wherein the zinc compound is present in an amount of about 5%.

11. The method of claim 7 wherein the zinc compound is zinc oxide.

* * * * *